(12) United States Patent
Arnold et al.

(10) Patent No.: US 8,293,960 B2
(45) Date of Patent: Oct. 23, 2012

(54) PROCESS FOR THE PRODUCTION OF BUTADIENE

(75) Inventors: Stephen Craig Arnold, Mountain Lakes, NJ (US); Anne Mae Gaffney, West Chester, PA (US); Lawrence John Karas, Spring, TX (US); Philip Jay Angevine, Woodbury, NJ (US); Chuen Yuan Yeh, Edison, NJ (US); Ruozhi Song, Wilmington, DE (US)

(73) Assignee: Lummus Technology Inc., Bloomfield, NJ (US)

( * ) Notice: Subject to any disclaimer, the term of this patent is extended or adjusted under 35 U.S.C. 154(b) by 308 days.

(21) Appl. No.: 12/542,565

(22) Filed: Aug. 17, 2009

(65) Prior Publication Data

US 2011/0040134 A1 Feb. 17, 2011

(51) Int. Cl.
C07C 5/22 (2006.01)
C07C 5/32 (2006.01)

(52) U.S. Cl. ......... 585/324; 585/633; 585/627; 585/664
(58) Field of Classification Search ................. None
See application file for complete search history.

(56) References Cited

U.S. PATENT DOCUMENTS

| | | | |
|---|---|---|---|
| 2,403,672 A * | 7/1946 | Matuszak ............... 585/664 |
| 2,416,647 A * | 2/1947 | Schulze et al. ........... 585/627 |
| 3,531,545 A | 9/1970 | Garner et al. |
| 3,668,147 A | 6/1972 | Yoshino et al. |
| 3,764,632 A | 10/1973 | Takenaka et al. |
| 4,132,745 A | 1/1979 | Amigues et al. |
| 4,547,615 A | 10/1985 | Yamamoto |
| 5,087,780 A * | 2/1992 | Arganbright ............ 585/259 |
| 5,157,194 A | 10/1992 | Rahmim et al. |
| 6,242,661 B1 * | 6/2001 | Podrebarac et al. ...... 585/664 |
| 6,743,958 B2 | 6/2004 | Commereuc et al. |
| 6,849,773 B2 | 2/2005 | Podrebarac et al. |
| 6,916,448 B2 * | 7/2005 | Commereuc et al. ...... 422/134 |

(Continued)

FOREIGN PATENT DOCUMENTS

JP 2005-200364 7/2005

(Continued)

OTHER PUBLICATIONS

Newman, "Process for Butadiene Manufacture by Catalytic Oxydehydrogenation of Butenes", Journal of Industrial and Engineering Chemistry, vol. 62, No. 5, May 1970, pp. 42-47.

(Continued)

Primary Examiner — Tam M Nguyen
(74) Attorney, Agent, or Firm — Alix, Yale & Ristas, LLP

(57) ABSTRACT

Processes are provided for the production of butadiene from $C_4$ containing feed stocks that contain isobutene and/or isobutane in addition to n-butene(s) and/or n-butane. The processes of the present invention generally comprise feeding the feed stock to a combination butenes isomerization reaction and distillation tower for conversion of 1-butene to 2-butenes and separation from isobutene and isobutane, followed by an oxy-dehydrogenation unit to convert n-butenes to butadiene. The processes may also include additional isomerization and/or dehydrogenation steps for the tower overhead and bottoms streams to create additional isobutene and/or n-butenes for valued uses, which may include additional production of butadiene. The feed to the system may comprise any mixture or separate feeding of $C_4$ olefins and $C_4$ paraffins, at least one of which contains isobutene and/or isobutane.

17 Claims, 5 Drawing Sheets

U.S. PATENT DOCUMENTS

| | | |
|---|---|---|
| 7,034,195 B2 | 4/2006 | Schindler et al. |
| 7,488,857 B2 * | 2/2009 | Johann et al. ............... 585/325 |
| 7,888,541 B2 * | 2/2011 | Gartside et al. ............. 585/253 |
| 2004/0019245 A1 | 1/2004 | Gartside et al. |
| 2004/0077909 A1 * | 4/2004 | Commereuc et al. ......... 585/324 |
| 2005/0171311 A1 * | 8/2005 | Schindler et al. ............. 526/335 |
| 2005/0250969 A1 * | 11/2005 | Bridges ........................ 585/324 |
| 2006/0025641 A1 | 2/2006 | Gartside et al. |
| 2006/0235253 A1 * | 10/2006 | Gartside et al. ............. 585/664 |
| 2007/0179330 A1 | 8/2007 | Johann et al. |
| 2010/0041930 A1 * | 2/2010 | Gartside et al. ............. 585/314 |

FOREIGN PATENT DOCUMENTS

| | | |
|---|---|---|
| JP | 2005-200365 | 7/2005 |

OTHER PUBLICATIONS

International Search Report and Written Opinion for International Application No. PCT/US2010/002176.

* cited by examiner

PROCESS FOR THE PRODUCTION OF BUTADIENE

FIELD OF THE INVENTION

The present invention relates to improved processes for the production of butadiene. Processes are described for producing butadiene from $C_4$ feed stocks that contain a significant amount of isobutene and/or isobutane in addition to n-butene(s) and/or n-butane. Butadiene is produced by dehydrogenation of n-butenes incorporating the use of oxydehydrogenation, after highly efficient separation of isobutene (plus any isobutane) from all the n-butenes (plus any n-butane) by utilizing a combination butenes isomerization reaction and distillation tower. The process incorporates conversion of 1-butene to 2-butenes to accomplish substantially full iso/normal separation. The processes may be supplemented by additional isomerization and/or dehydrogenation steps for the tower overhead and bottoms streams and with additional feed streams.

BACKGROUND

Butadiene is a versatile raw material used in the production of a wide variety of synthetic rubbers, polymer resins and chemical intermediates. The largest uses for butadiene are the production of styrene butadiene rubber and polybutadiene rubber, which are used mainly in tire products. Butadiene is also one of the components used in the manufacture of acrylonitrile-butadiene-styrene, styrene-butadiene copolymer latex, styrene-butadiene block copolymers and nitrile rubbers.

There is a growing demand for butadiene caused by the growth in tire demand as well as reduced natural rubber production. World butadiene consumption is forecasted to grow at an average rate of about 2%+ per year.

The major source of butadiene is as a byproduct in the steam cracking of naphtha and gas oil to make ethylene and propylene. Steam cracking is a process by which hydrocarbon molecules are exposed to very hot steam, causing them to break apart into smaller molecules. Separation of butadiene from the other products of the steam cracking process typically includes the use of extractive distillation.

Other potential sources for the production of butadiene include converting feed stocks comprising butene and butane compounds and mixtures thereof to butadiene. Isobutene has been used for the synthesis of MTBE. The market for MTBE, however, is decreasing, especially in the United States. Thus, there is emerging a relative abundance of isobutene. The various $C_4$ streams represent alternative feed stocks for the production of butadiene. Unfortunately, industrial processes have not been developed or designed to effect efficient conversion and selectivity of butadiene from these sources, in particular when they contain a significant amount of isobutene and/or isobutane.

Various processes for butene isomerization are described in U.S. Pat. Nos. 3,531,545; 4,132,745; 5,157,194; and 6,743,958. The processes described in these patents are directed to butene isomerization reactions rather than production of butadiene.

"Reverse" isomerization of isobutene to n-butenes is described in Japanese Patent Application Nos. 2004-009136 and 2004-009138, and literature references Gon Seo et al., "The Reversible Skeletal Isomerization between n-Butenes and Iso-butene over Solid Acid Catalysts" Catalysis Today 44 (1998) 215-222, and Lucia M. Petkovic and Gustavo Larsen, "Linear Butenes from Isobutene over H-Ferrierite: In Situ Studies Using an Oscillating Balance Reactor", J. of Catalysis 191, 1-11 (2000). These processes are not directed to production of butadiene.

U.S. Pat. No. 6,743,958 to Commereuc et al. describes an integrated process including the separate steps of: (1) selective hydrogenation of butadiene with isomerization of 1-butene into 2-butenes; (2) the skeletal ("reverse") isomerization of isobutene into n-butenes; and (3) the metathesis of a 2-butene-rich fraction with ethylene. U.S. Pat. No. 5,157,194 to Rahmim et al. describes a method for the high level conversion of n-olefin-containing hydrocarbon streams to iso-olefin-rich product streams using a catalyst composition comprising microcrystalline ZSM-22.

Japanese Patent Application No. 2004-009136 describes isomerizing isobutene to n-butenes using ferrierite or γ-alumina. Japanese Patent Application No. 2004-009138 describes isomerizing isobutene to n-butenes using γ-alumina with water co-feed. U.S. Pat. Nos. 6,242,661 and 6,849,773 to Podrebarac et al., incorporated herein by reference in their entirety, describe the use of a combination butenes isomerization reaction and distillation tower to convert 1-butene to 2-butenes while fractionating to separate isobutene (and isobutane) from 2-butenes (and n-butane).

All of these references are generally directed to isomerization reactions or to utilizing the products for metathesis. None of these references include the dehydrogenation of $C_4$ compounds such as n-butenes to butadiene.

Hydrocarbon Processing, November 1978, pp 131-136 by PetroTex, describes the oxydehydrogenation of n-butenes to butadiene. However, this reference does not describe butene isomerization, "reverse" isomerization, or methods to reduce or eliminate the disadvantageous impacts of isobutene by removing it. In addition, this reference does not describe the transformation of the unwanted isobutene into additional productive n-butenes and obtaining supplemental production of butadiene by adding conversion of isobutene. Moreover, the oxydehydrogenation process described in this article has high costs due to the use of a very large amount of steam to dilute the mixture and limit the reaction temperature rise in an adiabatic packed bed reactor.

U.S. Pat. Nos. 3,668,147; 4,547,615; and 7,034,195, describe the general production of butadiene. U.S. Pat. No. 7,034,195 to Schindler et al. describes an integrated process for preparing butadiene from n-butane via (1) feeding n-butane into a first dehydrogenation zone, autothermally (i.e., with some exothermic oxygen reaction, e.g., combustion, to balance heat requirement but not as a direct oxidative dehydrogenation reaction) converting n-butane to 1-butene, 2-butenes and optionally butadiene, (2) feeding the first product gas stream into a second dehydrogenation zone, which does oxidatively convert 1-butene and 2-butenes to butadiene.

U.S. Pat. No. 4,547,615 to Yamamoto describes oxidative dehydrogenation of monoolefin to a conjugated $C_{4+}$ diolefin via a mixed metal oxide, with primary metals as Mo, Bi, Cr, Ni, etc. U.S. Pat. No. 3,668,147 to Yoshino et al. describes several reactions including butadiene production via mixed metal oxides, primarily Fe/Sb/V or Mo or W/Te/etc.

These references, however, do not describe industrial processes to efficiently and selectively produce butadiene from $C_4$ feed stocks that contain a significant amount of isobutene and/or isobutane. Butadiene production processes from these feed stocks must address, among other issues, the undesirability of isobutene in the dehydrogenation step to butadiene and the nearly identical volatilities of isobutene and 1-butene making them essentially impossible to separate by standard distillation. Of the four butene species (cis-2-butene, trans-2-butene, 1-butene and isobutene), isobutene does not substantially form butadiene via dehydrogenation and in oxydehydrogenation is reactive towards direct combustion and formation of some amount of undesirable oxygenated and other byproducts. This also results in increased oxygen consumption. In addition, it causes catalyst deactivation. Consequently, it is undesirable to have a significant amount of isobutene in the dehydrogenation feed. If present at a substantial level, isobutene in the feed stocks must be separated from the n-butenes and n-butane.

However, it is very difficult to completely separate isobutene from all the n-butenes by distillation. In particular, isobutene and 1-butene are considered "co-boilers" because they differ by less than 1° C. in boiling points, at about −6° C. at atmospheric pressure. The 2-butenes boil at 1-4° C. Accordingly, elimination of 1-butene by isomerizing it to 2-butenes enables enhanced separation of isobutene from n-butenes by distillation in accordance with the processes of the present invention.

In addition to obtaining benefit by excluding isobutene from the feed to the $nC_4$ dehydrogenation unit, an additional benefit can be obtained by converting the isobutene to additional n-butenes by "reverse" isomerization to augment the feed to the $nC_4$ dehydrogenation unit. Isobutene/n-butene isomerization has historically focused on isobutene formation because of the demand for MTBE. Because n-butenes are not typically sold commercially, there has been little incentive for research on the "reverse" conversion of isobutene to n-butenes.

Isobutane also does not form butadiene via its direct dehydrogenation, though it is not harmful in terms of reacting significantly to undesired byproducts. On the other hand, extra butadiene production can be obtained from isobutane if it is dehydrogenated to isobutene and then the isobutene undergoes the "reverse" isomerization described above, creating additional n-butenes that can eventually be converted to butadiene. Thus, a unit to dehydrogenate isobutane to isobutene may be added for this purpose in accordance with this invention.

A different dehydrogenation unit to convert n-butane to n-butenes and possibly some amount of butadiene may also be added to the overall process plant in accordance with the present invention.

While many industrial processes have been investigated for, and are related to, the production of butadiene, none have been developed and designed for the conversion of $C_4$ feed stocks containing a significant amount of isobutene and/or isobutane. As such, there exists an ongoing and unmet need in the industry for economical and efficient methods for butadiene production from these feed stocks.

SUMMARY OF THE INVENTION

The present invention relates generally to a method for the production of butadiene from mixed $C_4$ feed stocks after removing isobutene. The removal of isobutene is accomplished by the use of a combination butenes isomerization reaction and distillation tower. The isomerization reaction within the tower converts 1-butene to 2-butenes while fractionating to separate isobutene from 2-butenes. Any isobutane accompanies the isobutene in the overhead from the tower, while n-butane accompanies the 2-butenes in the tower bottoms. The conversion of the 1-butene to 2-butenes prevents the 1-butene from entering the tower overhead and allows it to be transferred in a productive form into the tower bottoms, where it is utilized in butadiene production without being accompanied by isobutene. An example of a combination butenes isomerization reaction and distillation tower is the "CDdeIB®" system by CDTECH, part of their CDHydro® Technologies, described in U.S. Pat. Nos. 6,242,661 and 6,849,773 referenced above. The catalyst used for the n-butenes isomerization reaction in the tower is preferably a 0.3-0.4 wt % Pd on alumina type catalyst.

The overhead from the (CDdeIB®) combination butenes isomerization reaction and distillation tower contains primarily isobutene and/or isobutane with only small amounts of n-butenes. The bottoms from the combination butenes isomerization reaction and distillation tower comprises primarily 2-butenes and any n-butane, with only small amounts of isobutene.

The tower bottoms is fed to one or more dehydrogenation reactor units for conversion of the 2-butenes, and if desired, n-butane, to butadiene. An oxydehydrogenation system is used for conversion of n-butenes to butadiene. If a substantial amount of n-butane is present in the tower bottoms, or if there is n-butane supplied in a separate stream, an additional dehydrogenation unit may be added to convert it to n-butene by methods known to those skilled in the art, such as (i) by non-oxidative dehydrogenation using the Lummus CATADIENE® Process, (ii) by dehydrogenation processes including oxidatively "autothermal" dehydrogenation (wherein oxygen is typically added to combust some compound(s), e.g., hydrocarbon or preferably hydrogen generated by the dehydrogenation reaction, in sufficient quantity for its heat generation to satisfy the heat requirement of the endothermic dehydrogenation reaction that is the principal reaction), or (iii) by its own oxydehydrogenation. In all these cases in conjunction with the present invention, the dehydrogenation of the n-butane is utilized to produce primarily n-butenes that are then used in the final dehydrogenation reaction unit(s) to produce butadiene. Thus, there are two reaction steps from n-butane to n-butenes to butadiene rather than a single step directly from n-butane to butadiene. Depending on the amount of n-butane and other considerations, the system for the dehydrogenation of the n-butane may be upstream of the n-butenes oxydehydrogenation unit or downstream on the effluent $C_4$s from the n-butenes oxydehydrogenation unit after removal of the butadiene and any of its own recycle stream(s).

The CATADIENE® Process is capable of being utilized as a single reaction step by itself, accomplishing partial conversion of n-butane to n-butenes and partial further conversion to butadiene, with effluent n-butane and n-butenes both recycled after removal of product butadiene. However, due to the large recycles required, and the overall costs, it is more cost-effective to utilize a 2-step approach even with CATADIENE®, and feed the n-butenes produced there to the oxydehydrogenation process of the current invention.

As yet another option, and depending on the amount of n-butane and other factors, the additional dehydrogenation unit to convert the n-butane to n-butenes or butadiene may be omitted to forego that portion of the butadiene production process.

The overhead from the combination butenes isomerization reaction and distillation tower comprises primarily isobutene and possibly isobutane, plus any "light" compounds that are present. As an option for added value, the overhead stream may be fed to a "reverse" isomerization unit where the isobutene is partially converted to n-butenes, producing a mixed butenes stream. The mixed butenes stream may be fed back to the combination butenes isomerization reaction and distillation tower for conversion of its newly created 1-butene to 2-butenes and recovery of all newly created 2-butenes into the bottoms, as described above. Converting the isobutene and recycling its products in this manner increases the overall yield of the process and reduces or eliminates the discharge of the isobutene distillate.

When a substantial amount of isobutane is present, the isobutane will enter the overhead from the combination butenes isomerization reaction and distillation tower. In one embodiment, a dehydrogenation unit may be added to convert isobutane to isobutene by methods known to those skilled in the art, e.g., by non-oxidative dehydrogenation using the Lummus CATOFIN® Process, or by other types of dehydrogenation processes. This increases the content of isobutenes in the tower overhead stream, which may be exported if desired, or may be sent to a "reverse" isomerization unit as described above for converting the isobutene to n-butenes. The resulting mixed butenes may be fed to the combination butenes isomerization reaction and distillation tower, where 1-butene is converted to 2-butenes, the 2-butenes are recovered in the tower bottoms, and the n-butenes are then converted to butadiene in the n-butenes oxydehydrogenation unit.

As noted above, both the n-butenes oxydehydrogenation unit and, if present, the n-butane dehydrogenation unit may utilize recycle streams. In addition, recycle stream(s) and/or effluent stream from either may be sent to the other. Also, recycle stream(s) and/or effluent stream(s) from the dehydrogenation units may be recycled to the combination butenes isomerization reaction and distillation tower.

Butadiene and other effluent compounds may be recovered separately from the effluent of each of the dehydrogenation units or there may be recovery systems that are shared. Depending on compositions of the effluent streams, the effluent streams may be fed far upstream, e.g., to a butadiene extraction unit for the original $C_4$ stream from its source (steam cracker, FCC).

In one embodiment, the process of the present invention comprises feeding a mixture predominantly containing only n-butenes and isobutene into a combination butenes isomerization reaction and distillation tower capable of converting 1-butene to 2-butenes and distillation to separate isobutene from 2-butenes. The isomerization of 1-butene to 2-butenes allows better separation of the full amount of n-butenes in the feed from isobutene due to (i) sufficient boiling point difference between 2-butenes and isobutene and (ii) converting the 1-butene to 2-butenes to overcome the lack of a boiling point difference between 1-butene and isobutene. The overhead stream from the combination butenes isomerization reaction and distillation tower comprises primarily isobutene with only small amounts of n-butenes carried over, plus any "light" compounds that are present, including isobutane if present. The bottoms stream from the combination butenes isomerization reaction and distillation tower comprises primarily 2-butenes, with only small amounts of 1-butene and isobutene, plus any "heavy" compounds, including n-butane if present.

A portion of the overhead stream from the combination butenes isomerization reaction and distillation tower containing isobutene and any unconverted 1-butene may be used as direct reflux and the net overhead stream may be sent to storage or for further processing. For added value (unless isobutene product has higher value), a portion of the net overhead may be fed to a "reverse" isomerization unit where the isobutene is partially converted to n-butenes, producing a mixed butenes stream. The mixed butenes stream is fed back to the combination butenes isomerization reaction and distillation tower for conversion of its newly created 1-butene to 2-butenes and recovery of all newly created 2-butenes in the bottoms, as described above. Converting the isobutene and recycling its products in this manner increases the overall yield of the process and reduces or eliminates the discharge of the isobutene distillate.

A portion of the bottoms from the combination butenes isomerization reaction and distillation tower may be reboiled directly and part or all of the net bottoms is fed to one or more dehydrogenation reactor units for conversion of 2-butenes to butadiene. The butadiene product is separated and sent to storage or further processing. N-butenes that remain after the dehydrogenation unit(s) may be discharged in a purge stream and/or recycled to either the dehydrogenation unit(s) and/or the combination butenes isomerization reaction and distillation tower, with the preferred disposition depending on the composition of the n-butenes recycle stream, especially its content of compounds other than n-butenes.

In another embodiment of the processes of the present invention, a feed stream comprising mixed $C_4$ olefins (including isobutene as well as n-butenes) is fed to a combination butenes isomerization reaction and distillation tower capable of converting 1-butene to 2-butenes and distillation to separate isobutene from 2-butenes. In this embodiment of the invention, the feed stream further comprises a substantial amount of n-butane. The feed may also contain isobutane. The overhead from the combination butenes isomerization reaction and distillation tower comprises primarily isobutene and isobutane present in the feed, with only small amounts of other butenes. A portion of the overhead stream may be used as direct reflux and the net overhead stream may be sent to storage or further processing. Optionally, part or all of the net overhead stream may be fed to a "reverse" isomerization unit to partially convert the isobutene to n-butenes, producing a mixed butenes stream (plus the isobutane in the overhead), part or all of which may be recycled to the combination butenes isomerization reaction and distillation tower.

The bottoms from the combination butenes isomerization reaction and distillation tower comprises primarily n-butane and 2-butenes, with only small amounts of 1-butene and isobutene. In one embodiment, the bottoms contain less than 1 wt %, and preferably less than 0.5 wt %, isobutene. A portion of the bottoms may be reboiled directly and part or all of the net bottoms is fed to a first dehydrogenation reactor whose primary function is to partially convert the n-butane to n-butenes, while it may also convert a portion of n-butenes to butadiene. At least a portion of the n-butenes from the first dehydrogenation unit is fed to a second dehydrogenation unit which incorporates oxydehydrogenation of the n-butenes to butadiene. The first dehydrogenation reactor may be a CATADIENE® type reactor, in which case its product would normally include a significant amount of butadiene and the CATADIENE® unit could even be utilized as a single system to dehydrogenate both n-butane and n-butenes and ultimately produce butadiene without requiring a second reaction step. However, it is advantageous to operate the CATADIENE® unit in combination with an oxydehydrogenation unit and to utilize conditions in the CATADIENE® unit that maximize generation of n-butenes and minimize butadiene.

Butadiene produced in the first dehydrogenation reactor, such as the customized or mild CATADIENE® unit (which also might be called a CATOFIN® unit), may be separated and fed to the butadiene product line. Hydrogen may also be separated as a by-product for external or internal usage, and water may also be condensed and separated. Residual n-butane may be recycled to the first (n-butane) dehydrogenation unit and/or fed forward as a diluent to the second (n-butenes) oxydehydrogenation unit. Alternatively to these separations, part or all of the effluent from the n-butane dehydrogenation unit may be fed directly to the n-butenes oxydehydrogenation unit, if advantageous relative to accomplishing the separations between the two units. As an additional option, a combination of both approaches may be utilized. That is, a portion of the effluent from the n-butane dehydrogenation unit may be fed directly to the n-butenes oxydehydrogenation unit while a different portion may undergo separations before its n-butenes are also fed to the n-butenes oxydehydrogenation unit.

As described above, in one mode of operation, the first dehydrogenation unit obtains dehydrogenation of the n-butane content to n-butenes, while the second dehydrogenation unit uses oxydehydrogenation to convert the n-butenes to butadiene. An alternative operating scheme, which is especially useful when there are substantial n-butenes in the bottoms, is to reverse the order and dehydrogenate the n-butenes first, followed by dehydrogenation of the n-butane in the effluent hydrocarbon stream from the n-butenes oxydehydrogenation unit. The presence of the n-butane in the n-butenes oxydehydrogenation unit does not reduce the conversion of the n-butenes, and may be beneficial in diluting the exothermic reaction and avoiding flammable process mixtures by making the process mixture composition more hydrocarbon rich. It may be advantageous to build up the n-butane concentration by recycle.

Removing n-butenes present in the feed to the dehydrogenation units prior to dehydrogenating the n-butane and creating additional n-butenes, by converting them in the n-butenes oxydehydrogenation unit first, then removing the butadiene that is created, can be advantageous. The effluent $C_4$ stream from the n-butene oxydehydrogenation unit contains virtually all of the n-butane since it is essentially inert in the n-butenes oxydehydrogenation unit. With this order of dehydrogenation units, having only a minimal amount of butenes in the feed to the n-butane dehydrogenation unit reduces the interference of the n-butenes in the dehydrogenation of n-butane to n-butenes. In addition, the total hydrocarbon flow to the n-butane dehydrogenation unit becomes greatly reduced.

If the n-butane content in the feed stream and tower bottoms is low, it may be desirable to forego inclusion of the "first" dehydrogenation unit, and the butadiene production corresponding to conversion of the n-butane content, and revert to the embodiment that utilizes only the n-butenes oxydehydrogenation unit.

Depending on compositions, the separation of the butadiene in the effluents of the two dehydrogenation units may be accomplished in a shared butadiene separation system (e.g., extraction) or in a butadiene extraction unit for the original $C_4$ stream from its source (steam cracker, FCC).

In another embodiment of the invention, a first feed stream comprising mixed $C_4$ olefins is fed to a combination butenes isomerization reaction and distillation tower capable of converting 1-butene to 2-butenes and distillation to separate isobutene from 2-butenes. The feed may also contain n-butane and/or isobutane. A portion of the overhead may be used as direct reflux and the net overhead stream may be sent to storage or for further processing. For added value (unless isobutene product has higher value), a portion of the net overhead may be fed to a "reverse" isomerization unit and converted to a mixed $C_4$ olefin stream, plus any additional compounds, and partially or totally recycled to the combination butenes isomerization reaction and distillation tower as described above for other embodiments.

In this embodiment of the invention, a second, separate feed stream comprising n-butane, and without substantial n-butenes, is fed directly to a first dehydrogenation reactor capable of partially converting the n-butane to n-butenes, without feeding this n-butane through the combination butenes isomerization reaction and distillation tower. For this n-butane stream to bypass the combination butenes isomerization reaction and distillation tower, it needs to be essentially free of isobutene, although the stream may contain some amount of isobutane. The first dehydrogenation reactor may be a customized CATADIENE® type reactor as described above.

Where the tower bottoms stream does not contain a substantial amount of n-butane, the bottoms from the combination butenes isomerization reaction and distillation tower may bypass the first (n-butane) dehydrogenation reactor and may be fed directly to the second dehydrogenation reactor system to convert the n-butenes in the tower bottoms to butadiene. The second (n-butenes) dehydrogenation system incorporates use of oxydehydrogenation.

The effluent from the first (n-butane) dehydrogenation unit may be fed to the second (n-butenes) oxydehydrogenation unit directly or with some intermediate separations, recycle, etc. Each of the dehydrogenation units may have one or more effluent recycle streams, and the recycle streams may be recycled to the dehydrogenation unit feed, to the other dehydrogenation unit, or to the combination butenes isomerization reaction and distillation tower.

In an alternative embodiment of the process, the second feed stream, which comprises n-butane and is essentially free of isobutene, may also contain substantial n-butenes. Alternatively, the second (or a third) feed stream may comprise n-butenes without substantial n-butane and again be essentially free of isobutene. In these cases, as discussed for the previous embodiment, it may be desirable to feed the second (or third) feed stream first to the n-butenes oxydehydrogenation system, with the effluent $C_4$ stream from that unit then being fed to the n-butane dehydrogenation unit (i.e. the "second" dehydrogenation unit becomes followed by the "first").

In another embodiment, the first feed stream may contain a substantial amount of n-butane as well as mixed $C_4$ olefins. In this case, it may be advantageous to feed the net bottoms of the combination butenes isomerization reaction and distillation tower to the first (n-butane) dehydrogenation unit along with the second feed stream comprising n-butane and essentially no isobutene. Alternatively, the preferred processing scheme may be to send the net bottoms to the "second" (n-butenes) oxydehydrogenation unit followed by the "first" (n-butane) dehydrogenation unit.

In addition, there is the option to forego inclusion of the n-butane dehydrogenation unit altogether and utilize only the n-butenes oxydehydrogenation unit. As described previously, each of the dehydrogenation units may have its own recycle(s), and its recycle stream(s) may be sent to its feed, to the other dehydrogenation unit, or to the combination butenes isomerization reaction and distillation tower.

As described above, depending on compositions, the separation of the butadiene in the effluents of the two dehydrogenation units may be accomplished in a shared butadiene separation system (e.g., extraction), or one or more of the recycle or effluent streams may be fed to a butadiene extraction unit for the original $C_4$ stream from its source (steam cracker, FCC).

In another embodiment of the present invention, a feed stream comprising both mixed $C_4$ paraffins and mixed $C_4$ olefins, thus both isobutane and isobutene as well as n-butane and n-butenes, is fed to a combination butenes isomerization reaction and distillation tower capable of converting 1-butene to 2-butenes, and distillation to separate isobutane and isobutene from n-butane and 2-butenes. A portion of the overhead from the combination butenes isomerization reaction and distillation tower may be used as direct reflux and the net overhead stream may be sent to storage or for further processing. For added value (unless isoC$_4$ products have higher value), a portion of the net overhead may be fed to a "reverse" isomerization unit where the isobutene is partially converted to n-butenes, producing an isobutane plus mixed butenes stream. The isobutane plus mixed butenes stream is recycled and fed back to the combination butenes isomerization reaction and distillation tower for conversion of the 1-butene formed in the "reverse" isomerization unit to 2-butenes and recovery of the 2-butenes into the bottoms, as described above.

When the feed contains significant isobutane, the isobutane must be purged from the overhead system. This may be accomplished by simply purging a sufficient quantity of the overhead stream before or after the "reverse" isomerization unit, although this incorporates losses of isobutene and possibly n-butenes. Alternatively the isobutane may be purged by accomplishing further distillation to separate isobutane from isobutene, for example, isobutane as the overhead stream and isobutene as a side stream. Yet another option is to introduce on the overhead a dehydrogenation unit, such as a CATOFIN® unit, capable of converting isobutane to isobutene. The output from the isobutane dehydrogenation unit comprises a substantially increased level of isobutene, and at least a portion may be fed to a "reverse" isomerization unit capable of converting isobutene to mixed C$_4$ olefins. If isobutene is a desired product, a portion of the product of the isobutane dehydrogenation unit may be utilized for that purpose. The output from the "reverse" isomerization unit is fed back to the combination butenes isomerization reaction and distillation tower. Converting both the isobutane and isobutene and recycling their products in this manner obtains several increases in the overall yield of the butadiene process (and/or other dispositions of the n-butenes) and reduces or eliminates the discharge of the isoC$_4$ distillate.

The bottoms from the combination butenes isomerization reaction and distillation tower comprises 2-butenes and n-butane, with only small amounts of 1-butene and isobutene. A portion of the bottoms may be reboiled directly and part or all of the net bottoms may be fed to a first dehydrogenation reactor capable of converting the n-butanes to n-butenes. As described above, the first dehydrogenation reactor may be a CATADIENE® type reactor customized for use in the process. At least a portion of the n-butenes produced in the first dehydrogenation reactor is fed to the second dehydrogenation reactor system, which incorporates oxydehydrogenation where the n-butenes are converted to butadiene. If produced to a significant amount, as in a CATADIENE® unit, butadiene and/or hydrogen produced in the first (n-butane) dehydrogenation reactor, and water in its effluent, may be separated from the n-butenes in the effluent. The butadiene may be fed to the butadiene product line, and other separated compounds may be sent to their relevant dispositions before the n-butenes are fed to the second dehydrogenation reactor system. Alternatively, the effluent compounds from the n-butane dehydrogenation reactor system may be included, at least in part, in the feed to the n-butenes oxydehydrogenation reactor system without separation steps between the two dehydrogenation systems.

As discussed above, an alternative processing scheme can be to feed the net bottoms of the combination butenes isomerization reaction and distillation tower to the "second" (n-butenes) oxydehydrogenation unit, followed by feeding the effluent from the n-butenes oxydehydrogenation unit to the "first" (n-butane) dehydrogenation unit. In addition, there is the option to forego inclusion of the n-butane dehydrogenation unit altogether and utilize only the n-butenes oxydehydrogenation unit. As described previously, each of the dehydrogenation units may have its own recycle(s), and its recycle stream(s) may be sent to its feed, to the other dehydrogenation unit, or to the combination butenes isomerization reaction and distillation tower.

As described above, depending on compositions, the separation of the butadiene in the effluents of the two dehydrogenation units may be accomplished in a shared butadiene separation system (e.g., extraction), or one or more of the recycle or effluent streams may be fed to a butadiene extraction unit for the original C$_4$ stream from its source (steam cracker, FCC).

In another embodiment of the processes of the present invention, a feed stream comprising mixed C$_4$ paraffins, with or without substantial C$_4$ olefins, is fed to a distillation tower where isobutane is separated from n-butane. A portion of the overhead from the distillation tower may be used as direct reflux and the net overhead stream may be sent to storage or for further processing. At least a portion of the net overhead stream is fed to a dehydrogenation unit, such as a CATOFIN® unit, capable of converting isobutane to isobutene. At least a portion of the output from the isobutane dehydrogenation unit, now comprising substantial isobutene, is fed to a "reverse" isomerization unit capable of converting isobutene to mixed C$_4$ olefins. At least a portion of the output from the "reverse" isomerization unit, now comprising substantial newly created n-butenes that can add to the production of butadiene, is fed back to the distillation tower, which is now a combination butenes isomerization reaction and distillation tower processing a complete mixture of mixed C$_4$ paraffins and mixed C$_4$ olefins, that converts 1-butene to 2-butenes and distills to separate isobutane and isobutene from n-butane and 2-butenes.

The bottoms from the combination butenes isomerization reaction and distillation tower comprises n-butane, plus 2-butenes derived from dehydrogenation of isobutene in the overhead followed by its "reverse" isomerization and return to the tower. A portion of the bottoms may be reboiled directly and part or all of the net bottoms may be fed to a first dehydrogenation reactor capable of converting the n-butane to n-butenes. As described above, the first dehydrogenation reactor may be a CATADIENE® type reactor customized for use in the process. At least a portion of the n-butenes produced in the first dehydrogenation reactor is fed to the second dehydrogenation reactor system, which incorporates oxydehydrogenation where the n-butenes are converted to butadiene. If produced to a significant amount, as in a standard CATADIENE® unit, butadiene and/or hydrogen produced in the first (n-butane) dehydrogenation reactor, and water in its effluent, may be separated from the n-butenes in the effluent. The butadiene may be fed to the butadiene product line, and other separated compounds may be sent to their relevant dispositions before the n-butenes are fed to the second dehydrogenation reactor system. Alternatively, the effluent compounds from the n-butane dehydrogenation reactor system may be included, at least in part, in the feed to the n-butenes oxydehydrogenation reactor system without separation steps between the two dehydrogenation systems.

As discussed above, in an alternative processing scheme, the net bottoms of the combination butenes isomerization reaction and distillation tower is fed to the "second" (n-butenes) oxydehydrogenation unit, followed by feeding the effluent from the n-butenes oxydehydrogenation unit to the "first" (n-butane) dehydrogenation unit. In addition, there is the option to forego inclusion of the n-butane dehydrogenation unit altogether and utilize only the n-butenes oxydehydrogenation unit. As described previously, each of the dehydrogenation units may have its own recycle(s), and its recycle stream(s) may be sent to its feed, to the other dehydrogenation unit, or to the combination butenes isomerization reaction and distillation tower.

Depending on compositions, the separation of the butadiene in the effluents of the two dehydrogenation units may be accomplished in a shared butadiene separation system (e.g., extraction), or one or more of the recycle or effluent streams may be fed to a butadiene extraction unit for the original $C_4$ stream from its source.

It should be understood that the initial feed(s) to be processed, and also some recycle streams, may contain additional compounds besides the $C_4$ olefins and paraffins that have been discussed. These can include $C_4$ diolefins and acetylenic compounds, and also compounds other than $C_4$ hydrocarbons. Additional processing steps may be added, by methods known to those skilled in the art, to convert some of the compounds to additional $C_4$ olefins or paraffins, e.g., by selective hydrogenation, or to remove compounds as required for acceptable further processing.

One advantage of the present invention is an economical and efficient process configuration using a minimal number of steps to effect high conversion and butadiene selectivity of mixed $C_4$ (olefins and/or paraffins) feeds that contain a significant amount of isobutene and/or isobutane. This advantage is given by way of non-limiting examples only, and additional benefits and advantages will be readily apparent to those skilled in the art in view of the description set forth herein.

DETAILED DESCRIPTION OF THE INVENTION

Figure 1:
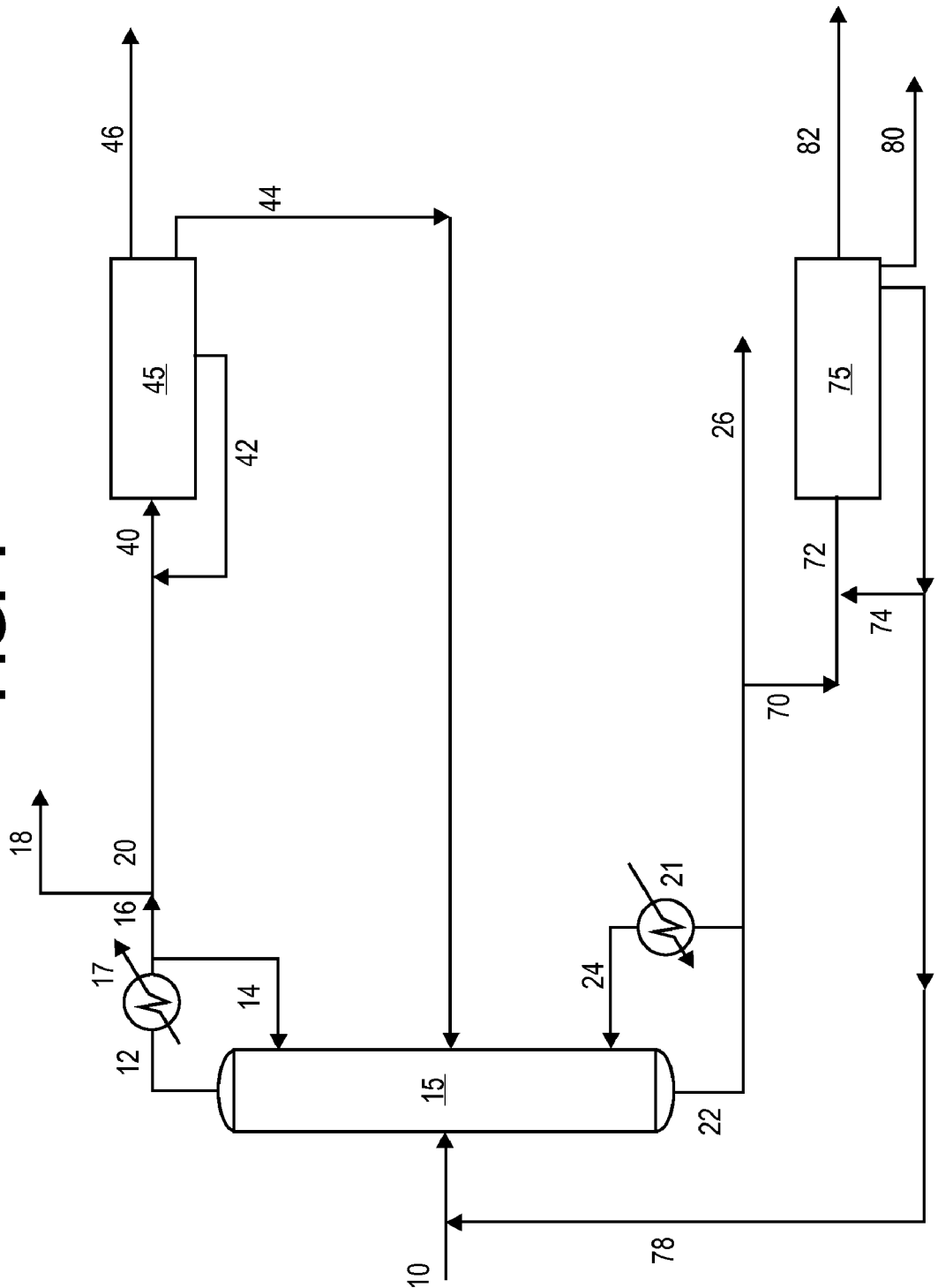
FIG. 1 is a flowchart showing one embodiment of the present invention wherein butadiene is produced by oxydehydrogenation of the n-butenes in the bottoms of a combination butenes isomerization reaction and distillation tower that is fed with a mixed $C_4$ olefin feedstock containing a significant amount of isobutene as well as n-butene(s).

The present invention relates to improved processes for the production of butadiene from $C_4$ feed stocks that contain a significant amount of isobutene and/or isobutane, via oxydehydrogenation after first removing isobutene without loss of 1-butene as valuable feed stock. A feed stream comprising a mixture of $C_4$ olefins is fed to a combination butenes isomerization reaction and distillation tower capable of converting 1-butene to 2-butenes and separating isobutene from 2-butenes by distillation. In some embodiments of the invention, the feed stream may further comprise $C_4$ paraffins.

The overhead from the combination butenes isomerization reaction and distillation tower contains primarily isobutene, with only small amounts of n-butenes. Any isobutane would also be present. Optionally, isobutene in the overhead stream may be partially converted to n-butenes by feeding the overhead stream to a "reverse" isomerization unit to convert the isobutene to a mixed $C_4$=stream. The output from the "reverse" isomerization unit is then fed back to the combination butenes isomerization reaction and distillation tower, as an additional source of n-butenes for producing the butadiene.

The bottoms from the combination butenes isomerization reaction and distillation tower comprises primarily 2-butenes with only small amounts of other butenes. Any n-butane would also be present. The bottoms are fed to an oxydehydrogenation unit, where the n-butenes present in the bottoms are converted to butadiene.

In another embodiment of the invention, as described in detail below, a significant amount of n-butane may be included in the feed to the combination butenes isomerization reaction and distillation tower, in addition to mixed butenes. The overhead from the tower is as described in the first embodiment, while the bottoms from the combination butenes isomerization reaction and distillation tower may be fed to a first dehydrogenation unit, such as for example a customized CATADIENE® type unit, where the n-butane is partially converted to n-butenes and some portion of the n-butenes may be partially converted to butadiene. The output from the first dehydrogenation unit may be separated into a butadiene product stream and an n-butene stream that is fed to a second dehydrogenation unit, which incorporates the use of oxydehydrogenation to convert the n-butenes to butadiene. Hydrogen produced in the first dehydrogenation unit may also be separated, as well as water in its effluent. Optionally, the output from the first dehydrogenation unit may be fed directly to the oxydehydrogenation unit without intermediate separations.

Alternatively, in one embodiment, the bottoms from the combination butenes isomerization reaction and distillation tower may be fed to the second dehydrogenation unit first, and thereafter a portion of the effluent from the second dehydrogenation unit may be fed to the first dehydrogenation unit.

Another option with this feed mixture (n-butane together with mixed butenes) is to forego inclusion of the "first" dehydrogenation unit, and the butadiene production corresponding to conversion of the n-butane content, and utilize only the n-butenes oxydehydrogenation unit.

In another embodiment, a stream containing n-butane and essentially no isobutene may be fed in a separate stream from the mixed butenes feed that does contain significant isobutene and is being processed in a combination butenes isomerization reaction and distillation tower. The separate n-butane stream may be sent directly to a first dehydrogenation unit to convert the n-butanes to n-butenes (and possibly some butadiene). In this case, the bottoms from the combination butenes isomerization reaction and distillation tower may be sent along with the output from the first dehydrogenation unit, to the second dehydrogenation unit to convert the n-butenes to butadiene using oxydehydrogenation.

If a separate n-$C_4$ feed stream contains substantial n-butenes, with or without n-butane, but still does not contain significant isobutene and require processing in the combination butenes isomerization reaction and distillation tower, it may be sent to the n-butenes oxydehydrogenation unit first, and thereafter a portion of the effluent from the n-butenes oxydehydrogenation unit may be sent to the n-butane dehydrogenation unit.

If a mixed butenes feed stream containing significant isobutene and being processed in the combination butenes isomerization reaction and distillation tower also contains significant n-butane, the bottoms of the tower may be sent first to the second dehydrogenation unit (oxydehydrogenation of n-butenes) as stated, or conversely, to the first dehydrogenation unit (dehydrogenation of n-butane) depending on composition and other factors.

As with the previous embodiment, an additional option with this total feed mixture (n-butane and mixed butenes) is to forego inclusion of the "first" dehydrogenation unit, and the butadiene production corresponding to conversion of the n-butane content, and utilize only the n-butenes oxydehydrogenation unit.

In yet another embodiment, a feed stream comprising both mixed $C_4$ paraffins and mixed $C_4$ olefins is fed to the combination butenes isomerization reaction and distillation tower where 1-butene is converted to 2-butenes, and isobutane and isobutene are separated from n-butane and 2-butenes. Optionally, the isobutene in the overhead may be partially converted to n-butenes using a "reverse" isomerization unit. The mixed $C_4$=stream is recycled back to the combination butenes isomerization reaction and distillation tower. Because the feed has significant isobutane, the isobutane must be purged from the overhead system. This may be accomplished by simply purging a sufficient quantity of the overhead stream before or after the "reverse" isomerization unit, although this will also result in losses of isobutene and possibly n-butenes. Alternatively the isobutane may be purged by accomplishing further distillation to separate isobutane from isobutene, for example, isobutane as the overhead stream and isobutene as a side stream. Yet another option is to introduce an isobutane dehydrogenation unit on the overhead to partially convert the isobutane to isobutene, then feed the effluent of that unit to the "reverse" isomerization unit. With this combination of units, nearly all the iso$C_4$s, saturated as well as unsaturated, can be transformed into n-butenes and ultimately butadiene.

In this embodiment, the bottoms from the combination butenes isomerization reaction and distillation tower, comprising 2-butenes and n-butane, may be processed as in the previous two embodiments.

In still another embodiment of the processes of the present invention, a feed stream comprising mixed $C_4$ paraffins, with or without substantial olefins, is fed to a combination butenes isomerization reaction and distillation tower where isobutane is separated from n-butane. The overhead from the combination butenes isomerization reaction and distillation tower is fed to a dehydrogenation unit to partially convert the isobutane to isobutene and its product is fed to a "reverse" isomerization unit capable of partially converting isobutene to mixed $C_4$ olefins. The output from the "reverse" isomerization unit is fed back to the combination butenes isomerization reaction and distillation tower, which now contains 2-butenes and also 1-butene to convert to 2-butenes, as well as isobutene to distill back to the overhead, in addition to the original mixed $C_4$ paraffins. The bottoms from the combination butenes isomerization reaction and distillation tower comprises n-butane and 2-butenes, and may be processed as in the previous embodiments containing these compounds.

FIG. 1 shows one embodiment of the present invention wherein butadiene is produced from a mixed $C_4$ olefin feed stream (10). The mixed $C_4$ olefin feed stream generally comprises isobutene, 1-butene and 2-butenes, which may be present in the feed stream in any proportions. Isobutene and 1-butene have very similar boiling points and are commonly referred to as "co-boilers." Both boil at approximately −6° C. at atmospheric pressure. Separation of the two is difficult by distillation alone. On the other hand, the 2-butenes boil at approximately 1-4° C. To capitalize on this enhanced difference relative to isobutene, the 1-butene is isomerized to 2-butenes in the combination butenes isomerization reaction and distillation tower (15), which enables separation of isobutene from all the n-butenes by distillation and increases the yield and selectivity of the process.

The mixed $C_4$ olefin feed stream (10) is fed into the combination butenes isomerization reaction and distillation tower (15) to convert 1-butene in the feed stream to 2-butenes. An example of this combination butenes isomerization reaction and distillation system is the "CDdeIB®" system by CDTECH, part of their CDHydro® Technologies. The 2-butenes in the mixture are separated from the isobutene and residual 1-butene by distillation. The overhead stream (12) from the combination butenes isomerization reaction and distillation tower (15) contains substantially all of the isobutene from the feed stream, with small amounts of n-butenes. Typically, the overhead stream comprises 5% or less by weight nC4s (n-butane plus n-butenes). The bottoms (22) from the combination butenes isomerization reaction and distillation tower (15) is comprised substantially of 2-butenes, with only small amounts of 1-butene or isobutene. Typically, the bottoms stream comprises 1% or less by weight iC4s (isobutane plus isobutene) and 1-5% or less by weight 1-butene.

The combination butenes isomerization reaction and distillation tower (15) includes a catalyst. The catalyst may be selected from any known catalyst used in the industry for the olefin isomerization. In some embodiments, the catalyst is Pd. In a particular embodiment, the catalyst is 0.3-0.4 wt % Pd on alumina.

Typically, the combination butenes isomerization reaction and distillation tower (15) is operated at a pressure of between 50 psig and 110 psig. The overhead stream exits the combination butenes isomerization reaction and distillation tower (15) at a temperature of between 80° F. and 180° F., and the bottoms stream exits the combination butenes isomerization reaction and distillation tower (15) at a temperature of between 100° F. and 250° F. Heat for the distillation process may be provided by any means known to those skilled in the art, such as by use of a reboiler.

The overhead stream (12) is typically condensed in a reflux condenser (17) and a portion is typically returned to the combination butenes isomerization reaction and distillation tower (15) as reflux (14), at a ratio of 0.5 to 33. If desired, a portion of the net overhead (16), i.e., the overhead stream (12) less the reflux stream (14), may be discharged from the plant for disposal, storage or further processing through line (18). It should be understood that line (18) may represent a single line or several different lines, possibly with different compositions.

Optionally, a portion of the net overhead stream (20) may undergo further processing and be recycled to the combination butenes isomerization reaction and distillation tower (15). In this embodiment, a portion of the net overhead stream is fed through line (40) to a "reverse" isomerization unit (45) to convert isobutene to n-butenes, creating a mixed $C_4$=stream. The "reverse" isomerization unit may be of any type known to those skilled in the art. Part or all of the output from the "reverse" isomerization unit (45) is fed through line (44) back into the combination butenes isomerization reaction and distillation tower (15). Optionally, part of the output from the "reverse" isomerization unit (45) may be sent to other dispositions through line (46), may represent several lines to several destinations, and some portion of the effluent of the "reverse" isomerization unit (45) may be recycled through line (42) back to the "reverse" isomerization unit feed stream (40).

A portion of the bottoms stream (22) from the combination butenes isomerization reaction and distillation tower (15), comprising 2-butenes, is typically reboiled directly in reboiler (21) and fed (24) back to the tower. A portion of the net bottoms (bottoms stream (22) less portion fed back to tower (24)) may be discharged from the plant for storage or further processing (26). Part or all of the net bottoms is fed through line (70) to the feed (72) to an oxydehydrogenation unit (75) to convert the 2-butenes to butadiene. The oxydehydrogenation unit (75) may be any type known to those skilled in the art for conversion of olefins to dienes.

The oxydehydrogenation unit (75) includes a catalyst. Any catalyst used for conversion of olefins to dienes may be used. The catalysts which are particularly suitable for the oxydehydrogenation of the n-butenes to 1,3-butadiene are generally based on Mo—Bi mixed metal oxide systems. Their preparations are described, for example, in U.S. Pat. No. 3,911,039 ($Mo_{12}BiFe_3Co_{4.5}Ni_{2.5}Sn_{0.5}K_{0.1}O_x$), U.S. Pat. No. 4,424,141 ($Mo_{12}BiFe_3Co_{4.5}Ni_{2.5}P_{0.5}K_{0.1}O_x$), U.S. Pat. No. 4,547,615 ($Mo_{12}BiFe_{0.1}Ni_8ZrCr_3K_{0.2}O_x$), U.S. Pat. No. 7,034,195 ($Mo_{12}Bi_{0.6}Fe_3Co_7Cr_{0.5}Si_{1.6}K_{0.08}O_x$), U.S. Pat. No. 4,423,281 ($Mo_{12}BiCr_3Ni_8Li_2Pb_{0.5}O_x$), and U.S. Pat. No. 4,336,409 ($Mo_uBiCr_3Ni_6P_{0.5}Cd_2FeO_x$). In the process according to the invention, preferred catalyst systems are described, for example, in U.S. Pat. No. 3,911,039 ($Mo_{12}BiFe_3Co_{4.5}Ni_{2.5}Sb_{0.5}K_{0.1}O_x$) and U.S. Pat. No. 7,034,195 ($Mo_{12}Bi_{0.6}Fe_3Co_7Cr_{0.5}Si_{1.6}K_{0.08}O_x$).

The oxydehydrogenation unit (75) preferably operates at a pressure of between 0 psig and 100 psig, and a temperature of between 550° F. and 850° F. The butadiene produced in the oxydehydrogenation unit (75) is separated from other effluent compounds by methods known to those skilled in the art, e.g., incorporating extractive distillation. Any residual n-butenes, plus other compounds useful to be recycled, e.g., n-butane and other non-reactive paraffins as diluents for the reaction, may be recycled to the oxydehydrogenation unit (75). The residual n-butenes may be recycled through line (74) to combine with the feed to the oxydehydrogenation unit (75) in feed stream (72) or through line (78) to combine with the feed stream (10) to the combination butenes isomerization reaction and distillation tower (15). By-products and unreacted compounds, etc., are purged from the system through discharge line(s) (80), which may constitute one line or several lines, possibly with different compositions. Recycle via line (78) to the combination butenes isomerization reaction and distillation tower (15) rather than or in addition to line (74) may be another path to remove quantities of $iC_4$s and lighter compounds that might accompany desirable recycle compounds. If both lines (74) and (78) are utilized, they may have different compositions. The butadiene product is fed through line (82) for storage or further processing.

Figure 2:
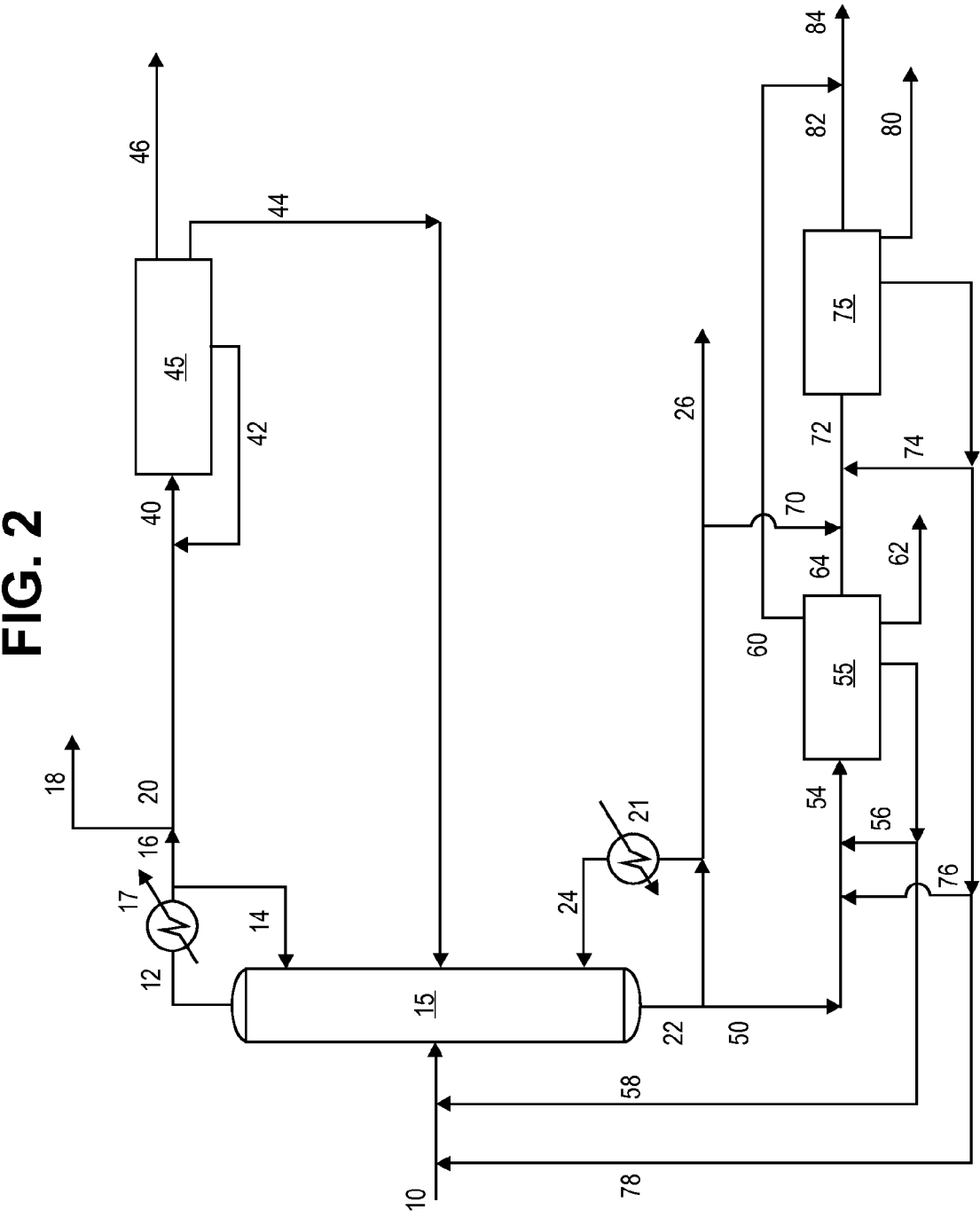
FIG. 2 is a flowchart showing another embodiment of the present invention wherein butadiene is produced by oxydehydrogenation of the n-butenes in the bottoms of a combination butenes isomerization reaction and distillation tower that is fed with a feed stream comprising mixed $C_4$ olefins together with n-butane.

In another embodiment of the invention shown in FIG. 2, butadiene is produced from a feed stream (10) comprising n-butane in addition, to mixed $C_4$ olefins. The feed stream may also contain isobutane. The feed stream (10) is fed into a combination butenes isomerization reaction and distillation tower (15) of the type described above. The 1-butene in the feed stream is converted to 2-butenes in an isomerization reaction on catalyst inside the tower. The overhead stream (12) from the combination butenes isomerization reaction and distillation tower (15) contains substantially all of the isobutene from the feed stream plus any isobutane that is present, with only small amounts of n-butenes and n-butane. Typically, the overhead stream comprises 5% or less by weight $cC_4$ (n-butane plus n-butenes). The bottoms (22) from the combination butenes isomerization reaction and distillation tower (15) is comprised substantially of 2-butenes and n-butane, with only small amounts of 1-butene or isobutene. Typically, the bottoms stream comprises 1% or less by weight iC4s (isobutene plus isobutene) and 1-55 or less by weight 1-butene.

A portion of the overhead stream is typically returned to the combination butenes isomerization reaction and distillation tower (15) as reflux (14). A portion of the net overhead (16), i.e., the overhead stream (12) less the reflux stream (14), may be discharged from the plant for disposal, storage or further processing through line(s) (18). Optionally, all or a portion of the net overhead stream (20) may undergo further processing and be recycled to the combination butenes isomerization reaction and distillation tower (15) as described above and as follows. The portion of the net overhead stream (20) being recycled is fed through line (40) to a "reverse" isomerization unit (45) to convert isobutene to n-butenes. Part or all of the output from the "reverse" isomerization unit (45) may be fed through line (44) back to the combination butenes isomerization reaction and distillation tower (15). If desired, part of the output from the "reverse" isomerization unit may be sent to other dispositions through line(s) (46), and some portion of the effluent of the "reverse" isomerization unit (45) may be recycled back to the feed stream (40) for the "reverse" isomerization unit through line (42).

The bottoms (22) from the combination butenes isomerization reaction and distillation tower (15) comprises 2-butenes and n-butane. A portion of the bottoms is typically reboiled in reboiler (21) and fed back to the tower (15) through line (24). A portion of the net bottoms may be discharged from the plant for storage or further processing through line (26). Part or all of the net bottoms may be fed through line (50) to the feed (54) to a first dehydrogenation unit (55) capable of partially converting the n-butane to n-butenes. Optionally, the dehydrogenation unit (55) may be configured to also convert n-butenes to butadiene. The first dehydrogenation unit (55) may incorporate a CATADIENE® type reactor, in which case its product would normally include a significant amount of butadiene, but the CATADIENE® unit may be operated to utilize conditions that maximize generation of n-butenes and minimize butadiene. In such an operation mode, might be called a CATOFIN® unit or it might still be called a (mild) CATADIENE® unit. At least a portion of the n-butenes produced in the n-butane dehydrogenation reactor (55) is fed through line (64) to an oxydehydrogenation reactor (75) of the type described above, where the n-butenes are converted to butadiene.

Butadiene produced in the first dehydrogenation unit (55) may be separated and fed through line (60) to the butadiene product line (84). Hydrogen may also be separated and removed as a by-product through (62) for external or internal usage. Water may be condensed, separated and removed through line (62). Some portion of the n-butenes may be discharged (62) if desired for use other than conversion to butadiene. It should be understood that line (62) may represent a single line or several different lines, possibly with different compositions, for removal of some product, by-products or unreacted feed components. Residual n-butane and other compounds may be separated and recycled to the first dehydrogenation unit (55) through line (56). Alternatively or in addition, a portion of the residual n-butane may be recycled by combining it with the feed stream (10) to the combination butenes isomerization reaction and distillation tower (15) through line (58), especially if there are any iC$_4$s or lighter compounds to purge via that route. In another embodiment, some portion of the residual n-butane is fed forward through line (64), together with or separately from the n-butenes, to the second dehydrogenation unit (75).

In another embodiment, part or all of the effluent from the first dehydrogenation unit may be fed, without the separation of by-products and n-butane described above, directly through line (64) to the second dehydrogenation unit (75), if advantageous relative to accomplishing the separations between the two units. As an additional option, a combination of both approaches may be utilized. That is, a portion of the entire effluent from the first dehydrogenation unit may be fed directly through line (64) to the second dehydrogenation unit (75) while a different portion may undergo separations before its n-butenes are also fed through line (64) to the second dehydrogenation unit (75).

In the embodiments described above, the first dehydrogenation unit (55) obtains dehydrogenation of the n-butane content in the tower bottoms to n-butenes, while the second (n-butenes) dehydrogenation unit (75) converts the n-butenes to butadiene using oxydehydrogenation. In other embodiments of the process shown in FIG. 2, which are especially useful when there are substantial n-butenes in the tower bottoms stream, the order described above is reversed and at least a portion of the net bottoms from the combination butenes isomerization reaction and distillation tower (15) is fed through line (70) to dehydrogenate the n-butenes first in the oxydehydrogenation unit (75), followed by sending the n-butane portion of the effluent from the n-butenes oxydehydrogenation unit (75) to the n-butane dehydrogenation unit (55) through line (76) and/or possibly to the combination butenes isomerization reaction and distillation tower (15) through line (78). In this embodiment, the feed (72) to the n-butenes oxydehydrogenation unit (75) is a combination of direct bottoms from the combination butenes isomerization reaction and distillation tower (15) provided through line (70) together with n-butenes stream(s) (64) from the n-butane dehydrogenation unit (55). The total feed to the n-butenes oxydehydrogenation unit (75) may also include recycle (74) from its own effluent.

Alternatively, a first portion of the bottoms from the combination butenes isomerization reaction and distillation tower (15) may be fed to the n-butane dehydrogenation unit (55) through line (50) and a second portion of the bottoms from the combination butenes isomerization reaction and distillation tower (15) may be fed to the n-butenes oxydehydrogenation unit (75) through line (70).

In yet another embodiment (not shown in FIG. 2 but with the same configuration as depicted in FIG. 1), the n-butane dehydrogenation unit (55) and the butadiene production corresponding to conversion of the n-butane content may be foregone entirely, and the n-butenes oxydehydrogenation unit (75) may be used alone to convert n-butenes to butadiene, while the n-butane is purged through line (80).

Though not depicted in FIG. 2, the separation of the butadiene in the effluents of the two dehydrogenation units (55) and (75) may be accomplished in a shared butadiene separation system (e.g., extraction). If desired, one or more of the recycle or effluent streams may be fed far upstream, e.g., to a butadiene extraction unit for the original C$_4$ stream from its source (steam cracker, FCC).

Figure 3:
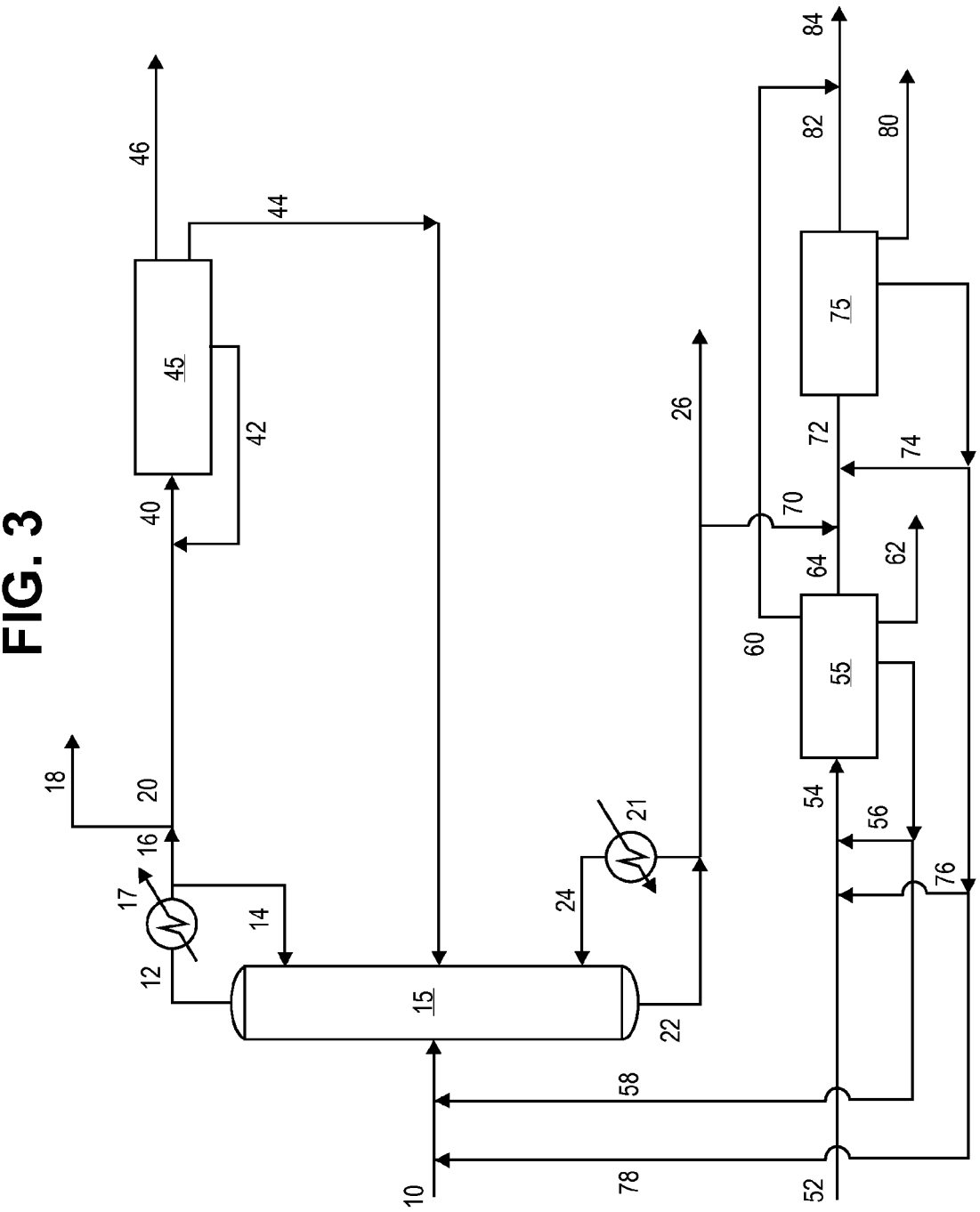
FIG. 3 is a flowchart showing another embodiment of the present invention in which a separate n-butane stream is fed to a dehydrogenation unit for conversion of n-butanes to n-butenes. Alternatively, a separate $nC_4$ stream may be fed first to the n-butenes oxydehydrogenation unit, especially if it comprises substantial content of n-butenes.

In another embodiment of the present invention shown in FIG. 3, a first feed stream (10) comprising a mixed C$_4$ olefin stream is fed to the combination butenes isomerization reaction and distillation tower (15) of the type described above, and a second feed stream (52) comprising n-butane and essentially free of isobutene is fed to an n-butane dehydrogenation unit (55) through line (54). As described above, in the combination butenes isomerization reaction and distillation tower (15), 1-butene in the first feed stream is converted to 2-butenes. The 2-butenes in the mixture are separated from the isobutene and residual 1-butene by distillation. The overhead stream (12) from the combination butenes isomerization reaction and distillation tower (15) contains substantially all of the isobutene, plus any isobutane that is present in the first feed stream, with only small amounts of n-butenes. The overhead stream is cooled in cooler (12). The bottoms (22) from the combination butenes isomerization reaction and distillation tower (15) is comprised substantially of 2-butenes, plus any n-butane that may be contained in the first feed stream, with only small amounts of 1-butene or isobutene.

A portion of the overhead stream (12) is typically returned to the combination butenes isomerization reaction and distillation tower (15) as reflux (14). A portion of the net overhead (16) may be discharged from the plant for disposal, storage or further processing through line(s) (18). Optionally, all or a portion of the net overhead stream (20) may undergo further processing and be recycled to the combination butenes isomerization reaction and distillation tower (15) as described above and as follows. The portion of the net overhead stream to be recycled is fed through line (40) to a "reverse" isomerization unit (45) to convert isobutene to n-butenes. Part or all of the output from the "reverse" isomerization unit (45) is fed through line (44) back to the combination butenes isomerization reaction and distillation tower (15). Part or all of the output may be sent to other dispositions (46), and some portion of the effluent of the "reverse" isomerization unit (45) may be recycled (42) back to the unit through feed line (40).

The bottoms (22) from the combination butenes isomerization reaction and distillation tower (15) comprises 2-butenes and any n-butane that is present. A portion of the bottoms is typically reboiled in reboiler (21) and fed back to the tower (15) through line (24). A portion of the net bottoms may be discharged from the plant for storage or further processing (26). Part or all of the net bottoms from the combination butenes isomerization reaction and distillation tower (15) may be fed through line (70) to the oxydehydrogenation unit (75) for conversion of the 2-butenes to butadiene.

The second feed stream (52) comprising n-butanes may be fed through line (54) to the first dehydrogenation unit (55) capable of partially converting the n-butane to n-butenes. Optionally, the first dehydrogenation unit (55) may be configured to also convert n-butenes to butadiene. The first dehydrogenation unit (55) may incorporate a CATADIENE® type reactor, in which case its product would normally include a significant amount of butadiene but the CATADIENE® unit may be operated to utilize conditions that maximize generation of n-butenes and minimize butadiene. In such an operation mode, the unit may be considered a CATOFIN® unit or it might still be considered a (mild) CATADIENE® unit. At least a portion of the output from the n-butane dehydrogenation unit (55) is fed through line (64), together with net bottoms (70) from the combination butenes isomerization reaction and distillation tower (15), in combined stream (72) to the oxydehydrogenation unit (75) where the n-butenes are converted to butadiene.

The effluents from the dehydrogenation units (55) and (75) may undergo alternative processing approaches as described above for the embodiments illustrated in FIG. 2. Butadiene produced in the first dehydrogenation unit (55) may be separated and fed through line (60) to the butadiene product line (84). Hydrogen may also be separated and removed as a by-product through (62) for external or internal usage. Water may be condensed, separated and removed through line (62). Some portion of the n-butenes may be discharged (62) if desired for use other than conversion to butadiene. It should be understood that line (62) may represent a single line or several different lines, possibly with different compositions, for removal of some n-butenes, by-products or unreacted feed components. Residual n-butane and other compounds may be separated and recycled to the first dehydrogenation unit (55) through line (56). Alternatively or in addition, a portion of the residual n-butane may be recycled by combining it with the feed stream (10) to the combination butenes isomerization reaction and distillation tower (15) through line (58). In another embodiment, some portion of the residual n-butane is fed forward through line (64), together with or separately from the n-butenes, to the second dehydrogenation unit (75).

In another embodiment, part or all of the effluent from the first dehydrogenation unit may be fed, without the separation of by-products and n-butane described above, directly through line (64) to the second dehydrogenation unit (75), if advantageous relative to accomplishing the separations between the two units. As an additional option, a combination of both approaches may be utilized. That is, a portion of the entire effluent from the first dehydrogenation unit may be fed directly through line (64) to the second dehydrogenation unit (75) while a different portion may undergo separations before its n-butenes are also fed through line (64) to the second dehydrogenation unit (75).

Figure 4:
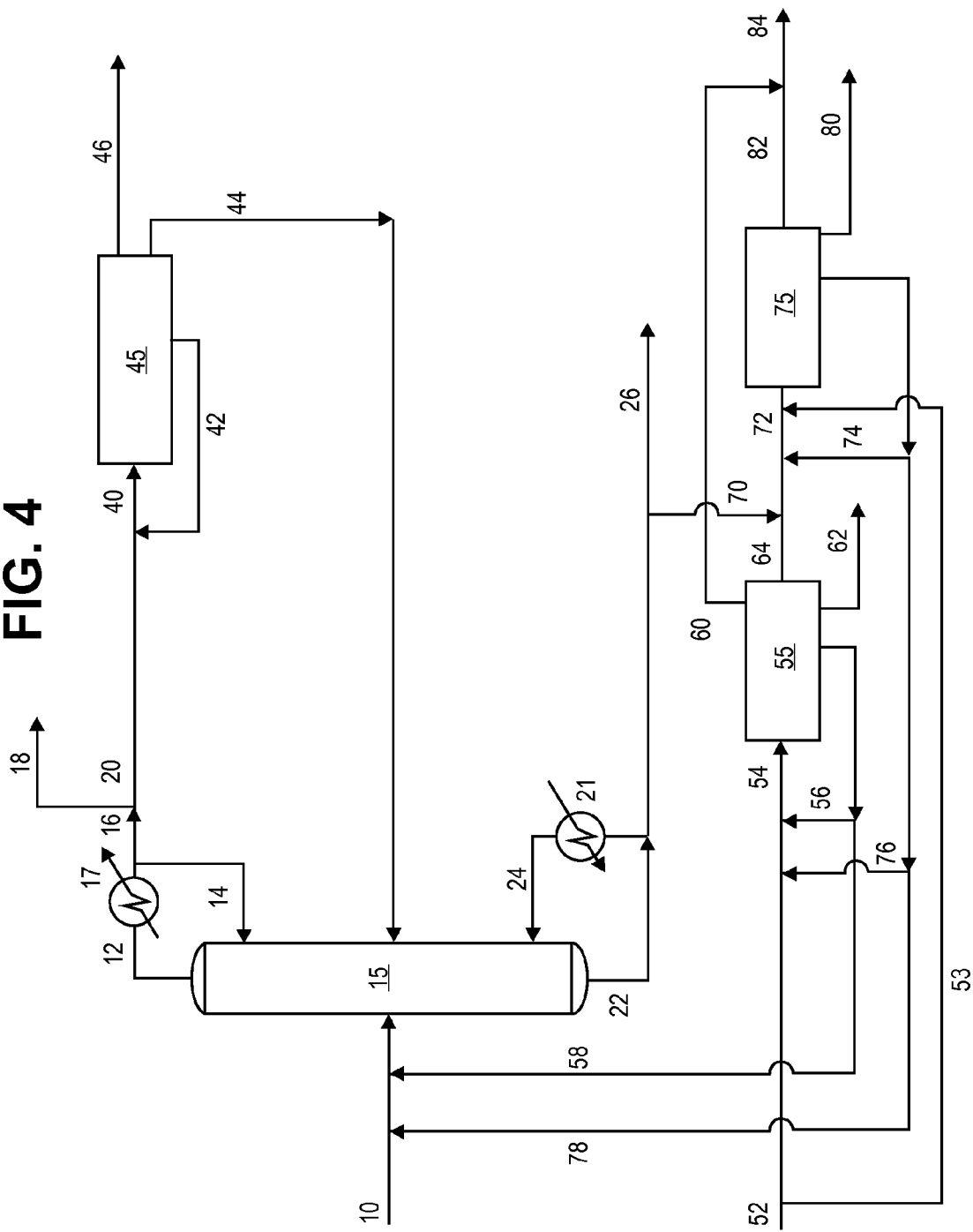
FIG. 4 is a flowchart showing an embodiment of the invention wherein all or part of a second feed stream containing n-butenes is fed directly to the oxydehydrogenation unit.

In the embodiments described above, the first dehydrogenation unit (55) obtains dehydrogenation of the n-butane content in the second feed stream (52) to n-butenes, while the second (n-butenes) oxydehydrogenation unit (75) converts the n-butenes to butadiene using oxydehydrogenation. In another embodiment of the process shown in FIG. 4, which is especially useful when there are substantial n-butenes in the second feed stream (52), the order described above is reversed and at least a portion of the second feed stream (52) is fed through line (53) to the feed line (72) to the oxydehydrogenation unit (75) to dehydrogenate the n-butenes in the feed stream (52) in the oxydehydrogenation unit (75), followed by sending the n-butane portion of the effluent from the n-butenes oxydehydrogenation unit (75) to the n-butane dehydrogenation unit (55) through line (76) as described above. In this embodiment, the feed to the n-butenes oxydehydrogenation unit (75) may be a combination of direct bottoms from the combination butenes isomerization reaction and distillation tower (15) provided through line (70) together with all or a portion of the second feed stream (52) and also n-butenes stream(s) (64) from the n-butane dehydrogenation unit (55). The total feed (72) to the n-butenes oxydehydrogenation unit (75) may also include recycle (74) from its own effluent as described above.

Alternatively, a first portion of the second feed stream (52) may be fed to the n-butane dehydrogenation unit (55) through line (54) and a second portion of the second feed stream (52) may be fed to the n-butenes oxydehydrogenation unit (75) through line (72). These two portions may have different compositions and be considered as a second and third feed stream.

In yet another embodiment (not shown), the n-butane dehydrogenation unit (55) and the butadiene production corresponding to conversion of the n-butane content may be foregone entirely, and the n-butenes oxydehydrogenation unit (75) may be used alone to convert n-butenes to butadiene, with the second feed stream (52) sent directly to the n-butenes oxydehydrogenation unit (75).

As described above, the separation of the butadiene in the effluents of the two dehydrogenation units (55) and (75) may be accomplished in a shared butadiene separation system (e.g., extraction). If desired, one or more of the recycle or effluent streams may be fed far upstream, e.g., to a butadiene extraction unit for the original $C_4$ stream from its source (steam cracker, FCC).

Figure 5:
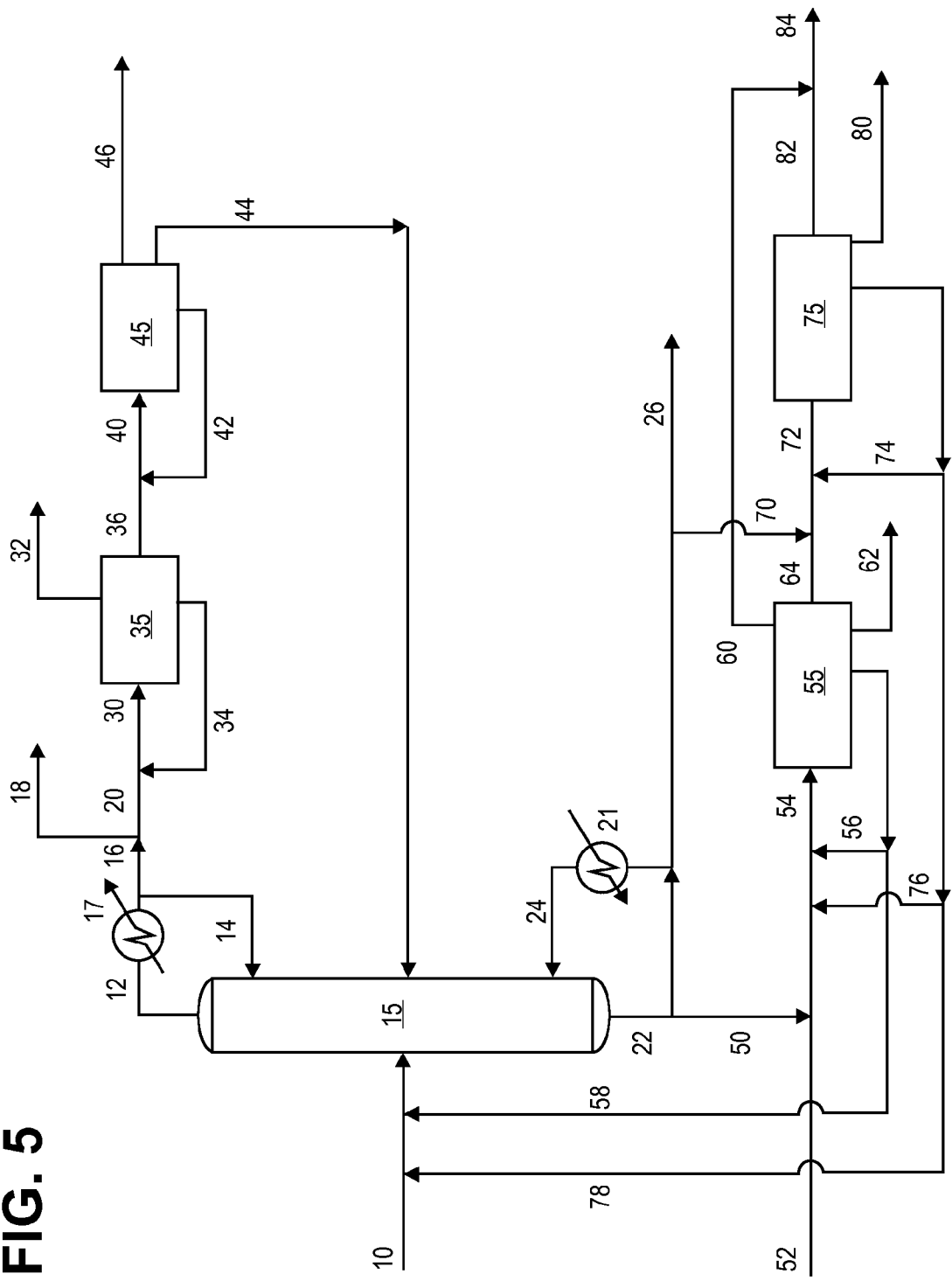
FIG. 5 is a flowchart showing another embodiment of the present invention wherein butadiene is produced by oxydehydrogenation of the n-butenes in the bottoms of a combination butenes isomerization reaction and distillation tower that is fed with a feed stream comprising both mixed $C_4$ olefins and mixed $C_4$ paraffins.

In another embodiment of the invention shown in FIG. 5, butadiene is produced from a feedstock comprising both mixed butenes and mixed butanes. The mixed $C_4$ feed stream is fed through line (10) to a combination butenes isomerization reaction and distillation tower (15) where 1-butene is converted to 2-butenes, and isobutane and isobutene are separated from n-butane and 2-butenes. A portion of the overhead stream (12) comprising isobutane and isobutene is typically returned to the combination butenes isomerization reaction and distillation tower (15) as reflux (14) after cooling in cooler (17). A portion of the net overhead (16), i.e., the overhead stream (12) less the reflux stream (14), may be discharged from the plant for disposal, storage or further processing (18).

Optionally, all or a portion of the net overhead stream (20) may undergo further processing and be recycled to the combination butenes isomerization reaction and distillation tower (15). In this embodiment, both isobutane and isobutene in the net overhead stream are transformed into compounds that can be converted to butadiene and recycled, by feeding a portion of the net overhead stream (20) through line (30) to a dehydrogenation unit (35), such as a CATOFIN® unit, capable of converting isobutane to isobutene. Some portion of the output from the dehydrogenation unit (35) may be discharged (32) and a second portion may be recycled to the inlet (30) of the isobutane dehydrogenation unit (35) through line (34). It should be understood that line (32) may represent a single line or several different lines, possibly with different compositions, for removal of some product, by-products or unreacted feed components.

At least a portion of the output (36) from the dehydrogenation unit (35) comprising substantially increased isobutene, is fed through line (40) to a "reverse" isomerization unit (45) capable of converting isobutene to n-butenes. Part or all of the output from the "reverse" isomerization unit (45) is fed through line (44) back to the combination butenes isomerization reaction and distillation tower (15). Part may be sent to other dispositions (46), and some portion of the effluent of the "reverse" isomerization unit (45) may be recycled (42) back to the unit through feed line (40). Optionally, a portion of the effluent from the dehydrogenation unit 35 is fed to the combination butenes isomerization reaction and distillation tower.

The bottoms from the combination butenes isomerization reaction and distillation tower (15) comprises 2-butenes and n-butane and may undergo any of the processing alternatives of the embodiments described above. Also, a second (or third) feed stream (52) comprising n-butane and/or n-butenes and essentially free of isobutene may be fed directly to an n-butane dehydrogenation unit (55) or the n-butenes oxydehydrogenation unit (75), as described above for FIG. 3 and using one of the processing alternatives described above.

In another embodiment of the processes of the present invention using the process equipment as illustrated in FIG. 5, a feed stream (10) comprising only mixed $C_4$ paraffins (i.e. without substantial $C_4=$) is fed to a combination butenes isomerization reaction and distillation tower (15) where isobutane is separated from n-butane. A portion of the overhead stream (12) is typically returned to the combination butenes isomerization reaction and distillation tower (15) as reflux (14) after cooling in cooler (17). A portion of the net overhead (16), i.e., the overhead stream (12) less the reflux stream (14), may be discharged from the plant for disposal, storage or further processing (18). In this embodiment, at least a portion of the net overhead (20) is transformed into compounds that can be converted to butadiene and recycled back to the combination butenes isomerization reaction and distillation tower (15). A portion of the net overhead stream (20) is fed through line (30) to a dehydrogenation unit (35), such as a CATOFIN® unit, capable of converting isobutane to isobutene. At least a portion of the output (36) from the dehydrogenation unit (35), comprising substantially increased isobutene, is fed through line (40) to a "reverse" isomerization unit (45) capable of converting isobutene to n-butenes. At least a portion of the output from the "reverse" isomerization unit is fed back to the combination butenes isomerization reaction and distillation tower (15) through line (44). Because stream (44) now contains some isobutene as well as n-butenes and some isobutane, the combination butenes isomerization reaction and distillation tower (15) now operates with a mixture of both mixed butanes and mixed butenes as in the previous embodiments and may undergo any of the processing alternatives of the embodiments described above.

The bottoms from the combination butenes isomerization reaction and distillation tower (15) comprises 2-butenes and n-butane and may undergo any of the processing alternatives of the embodiments described above.

One skilled in the art will recognize that numerous variations or changes may be made to the process described above without departing from the scope of the present invention. Accordingly, the foregoing description of preferred embodiments is intended to describe the invention in an exemplary, rather than a limiting sense.

Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

What is claimed is:

1. A process for the production of butadiene comprising the steps of:
   (a) feeding a first feed stream comprising a mixture of $C_4$ olefins to a combination butenes isomerization reaction and distillation tower to produce an overhead stream comprising isobutene and a bottoms stream comprising 2-butene;
   (b) feeding at least a portion of the bottoms stream to an oxydehydrogenation unit to convert the 2-butenes to butadiene;
   (c) separating the butadiene in the oxydehydrogenation unit effluent from unreacted compounds and by-products;
   (d) feeding at least a portion of the overhead stream to a reverse isomerization unit to convert isobutene to n-butene; and
   (e) feeding at least a portion of the effluent from the reverse isomerization unit to the combination butenes isomerization reaction and distillation tower.

2. The process of claim 1, further comprising the step of:
   (f) recycling at least a portion of the effluent from the oxydehydrogenation unit to the feed to the oxydehydrogenation unit.

3. The process of claim 1, further comprising the step of:
   (g) feeding at least a portion of the effluent from the oxydehydrogenation unit to the combination butenes isomerization reaction and distillation tower.

4. A process for the production of butadiene comprising:
   (a) feeding a first feed stream comprising a mixture of $C_4$ olefins to a combination butenes isomerization reaction and distillation tower to produce an overhead stream comprising isobutene and a bottoms stream comprising 2-butene;
   (b) feeding at least a portion of the bottoms stream to an oxydehydrogenation unit to convert the 2-butenes to butadiene;
   (c) separating the butadiene in the oxydehydrogenation unit effluent from unreacted compounds and by-products;
   (d) feeding a second feed stream comprising n-butanes to a first dehydrogenation unit to convert n-butanes to n-butenes;
   (e) feeding the effluent from the first dehydrogenation unit to the oxydehydrogenation unit;
   (f) feeding at least a portion of the overhead stream to a second dehydrogenation unit to convert isobutane to isobutene;
   (g) feeding at least a portion of the effluent from the second dehydrogenation unit to a reverse isomerization unit to convert isobutene to n-butenes; and
   (h) feeding at least a portion of the effluent from the second dehydrogenation unit to the combination butenes isomerization reaction and distillation tower.

5. The process of claim 4, further comprising the step of:
   (i) recycling at least a portion of the effluent from the oxydehydrogenation unit to the feed to the oxydehydrogenation unit.

6. The process of claim 4, further comprising the step of:
   (j) feeding at least a portion of the effluent from the oxydehydrogenation unit to the combination butenes isomerization reaction and distillation tower.

7. The process of claim 5, further comprising the step of:
   (j) feeding at least a portion of the effluent from the oxydehydrogenation unit to the combination butenes isomerization reaction and distillation tower.

8. The process of claim 1, further comprising:
   (h) feeding at least a portion of the bottoms stream to a first dehydrogenation unit to convert n-butanes to n-butenes, and
   (i) feeding at least a portion of the effluent from the first dehydrogenation unit to the oxydehydrogenation unit.

9. The process of claim 8, further comprising:
   (f) recycling at least a portion of the effluent from the oxydehydrogenation unit to the feed to the oxydehydrogenation unit.

10. The process of claim 8, further comprising the step of:
    (g) feeding at least a portion of the effluent from the oxydehydrogenation unit to the combination butenes isomerization reaction and distillation tower.

11. The process of claim 8, further comprising the step of:
    (j) recycling at least a portion of the effluent from the first dehydrogenation unit to the feed to the first dehydrogenation unit.

12. The process of claim 8, further comprising the step of:
(k) recycling at least a portion of the effluent from the first dehydrogenation unit to the combination butenes isomerization reaction and distillation tower.

13. The process of claim 8, further comprising the step of:
(l) feeding a second feed stream comprising n-butanes to the first dehydrogenation unit to convert n-butanes to n-butenes.

14. The process of claim 1, further comprising the step of:
(m) feeding at least a portion of the overhead stream to a second dehydrogenation unit to convert isobutane to isobutene.

15. The process of claim 14, further comprising the step of:
(n) feeding at least a portion of the effluent from the second dehydrogenation unit to the combination butenes isomerization reaction and distillation tower.

16. The process of claim 8, further comprising the step of:
(m) feeding at least a portion of the overhead stream to a second dehydrogenation unit to convert isobutane to isobutene.

17. The process of claim 16, further comprising the step of:
(n) feeding at least a portion of the effluent from the second dehydrogenation unit to the combination butenes isomerization reaction and distillation tower.

* * * * *